(12) United States Patent
Kashiwase

(10) Patent No.: US 11,647,911 B2
(45) Date of Patent: May 16, 2023

(54) MEASUREMENT APPARATUS AND MEASUREMENT METHOD

(71) Applicant: KYOCERA Corporation, Kyoto (JP)

(72) Inventor: Susumu Kashiwase, Machida (JP)

(73) Assignee: KYOCERA Corporation, Kyoto (JP)

( * ) Notice: Subject to any disclaimer, the term of this patent is extended or adjusted under 35 U.S.C. 154(b) by 606 days.

(21) Appl. No.: 16/637,204

(22) PCT Filed: Aug. 2, 2018

(86) PCT No.: PCT/JP2018/029049
§ 371 (c)(1),
(2) Date: Feb. 6, 2020

(87) PCT Pub. No.: WO2019/039223
PCT Pub. Date: Feb. 28, 2019

(65) Prior Publication Data
US 2020/0359907 A1     Nov. 19, 2020

(30) Foreign Application Priority Data

Aug. 25, 2017   (JP) .............................. JP2017-162250

(51) Int. Cl.
| | |
|---|---|
| *A61B 5/0205* | (2006.01) |
| *A61B 5/00* | (2006.01) |
| *A61B 5/1455* | (2006.01) |
| *A61B 5/0285* | (2006.01) |
| *A61B 5/026* | (2006.01) |

(52) U.S. Cl.
CPC .......... *A61B 5/0205* (2013.01); *A61B 5/0261* (2013.01); *A61B 5/0285* (2013.01); *A61B 5/14551* (2013.01); *A61B 5/6815* (2013.01); *A61B 5/742* (2013.01); *A61B 5/7405* (2013.01); *A61B 5/7455* (2013.01)

(58) Field of Classification Search
CPC .... A61B 5/0205; A61B 5/0285; A61B 5/1455
See application file for complete search history.

(56) References Cited

U.S. PATENT DOCUMENTS

| | | |
|---|---|---|
| 6,447,456 B1 | 9/2002 | Tsubata |
| 8,886,294 B2 * | 11/2014 | Lisogurski ........... A61B 5/0095 |
| | | 600/480 |
| 9,591,395 B2 | 3/2017 | Burgett et al. |

(Continued)

FOREIGN PATENT DOCUMENTS

| | | |
|---|---|---|
| JP | 2001-170016 A | 6/2001 |
| JP | 2003-225214 A | 8/2003 |

(Continued)

*Primary Examiner* — Gary Jackson
*Assistant Examiner* — Zahed Kabir
(74) *Attorney, Agent, or Firm* — Procopio Cory Hargreaves and Savitch LLP

(57) ABSTRACT

A measurement apparatus includes a plurality of sensors wearable on different parts of a human body and a controller configured to acquire an output value of each of the sensors. The sensor each outputs an output value to calculate the same type of biological information by optical measurement, the controller selects either the sensor on the basis of each output value of the sensors, and determines a measured value of the biological information on the basis of an output values of the sensors selected.

13 Claims, 10 Drawing Sheets

(56) References Cited

U.S. PATENT DOCUMENTS

| | | |
|---|---|---|
| 9,742,902 B2 | 8/2017 | Shimuta |
| 10,194,233 B2 | 1/2019 | Burgett et al. |
| 2013/0336495 A1 | 12/2013 | Burgett et al. |
| 2014/0106816 A1 | 4/2014 | Shimuta |
| 2015/0208933 A1* | 7/2015 | Satomi .................. A61B 5/6815 600/479 |
| 2017/0127174 A1 | 5/2017 | Burgett et al. |
| 2017/0196467 A1* | 7/2017 | Shiono ................. A61B 5/0261 |
| 2018/0317787 A1 | 11/2018 | Satomi et al. |
| 2019/0167123 A1* | 6/2019 | Hidaka ................ A61B 5/0245 |

FOREIGN PATENT DOCUMENTS

| | | |
|---|---|---|
| JP | 2010-4972 A | 1/2010 |
| JP | 2014-68733 A | 4/2014 |
| JP | 2015-521424 A | 7/2015 |
| JP | 2015-139516 A | 8/2015 |
| WO | 2009/001449 A1 | 12/2008 |
| WO | 2012/176371 A1 | 12/2012 |

\* cited by examiner

MEASUREMENT APPARATUS AND MEASUREMENT METHOD

CROSS-REFERENCE TO RELATED APPLICATION

This application claims priority to and the benefit of Japanese Patent Application No. 2017-162250 filed on Aug. 25, 2017, the entire disclosure of which being incorporated herein by reference.

TECHNICAL FIELD

This disclosure relates to a measurement apparatus and a measurement method.

BACKGROUND

As a method of measuring biological information, an optical measurement method is known in which a detected part is irradiated by using a light source such as an LED or a semiconductor laser to measure transmitted light, reflected light or scattered light (see, for example, patent literatures (PTL) 1 (JP2015-521424A) and PTL 2 (WO2009/001449A1)). For example, PTL 1 suggests that an optical physiological sensor is incorporated into an earphone to measure pulse and oxygen saturation. PTL 2 suggests that a self-light emitting sensor is incorporated into ear pads of a headphone to measure blood flow velocity, oxygen saturation and pulse. Furthermore, an apparatus for monitoring external light intensity (see, for example, PTL 3 (JP2010-004972A)) and an apparatus for setting data to valid/invalid on the basis of external light signal data (see, for example, PTL 4 (JP2015-139516A)) are also suggested.

SUMMARY

According to an aspect, the disclosed measurement apparatus includes a plurality of sensors and a controller. The sensors can be worn on different parts of a human body. The controller acquires an output value of each of the sensors. Each of the sensors outputs an output value to calculate the same type of biological information by an optical measurement. The controller selects any one of the sensors on the basis of the output value of each of the sensors. The controller determines the measurement value of the biological information on the basis of the output value of the sensor selected.

An aspect of the disclosed measurement method includes: wearing a plurality of sensors configured to perform an optical measurement of the same type of biological information on different parts of a user; and acquiring an output value of each of the sensors. According to an aspect, the measurement method further includes: selecting any one of the sensors on the basis of the output value and determining a measurement value of the biological information on the basis of the output value of the sensor selected.

DETAILED DESCRIPTION

When biological information is optically measured outdoors and an optical sensor is directed to the sun, a measurement may be made incorrectly due to sunlight. Therefore outdoor optical measurement requires countermeasures such as measurement under a sunshade tent, a subject wearing a wide-brimmed hat or covering an optical sensor with a hand and the like.

However, it is preferable that a measurement apparatus requires no additional equipment or facilities at the thought of use during mountain climbing or exercise. It is also preferable that, when a measurement is made continuously, it is not necessary for the user to pay no special attention to the measurement.

The measurement apparatus and a measurement method of this disclosure improve outdoor availability. In this context, the availability means an ability to use a measurement apparatus. The outdoor availability can be rephrased as environment resistance outdoors.

An embodiment of this disclosure will be described below with reference to the drawings. It is to be noted that drawings used for the description below are schematic drawings and are not necessarily to scale.

[Basic Configuration]

Figure 1:
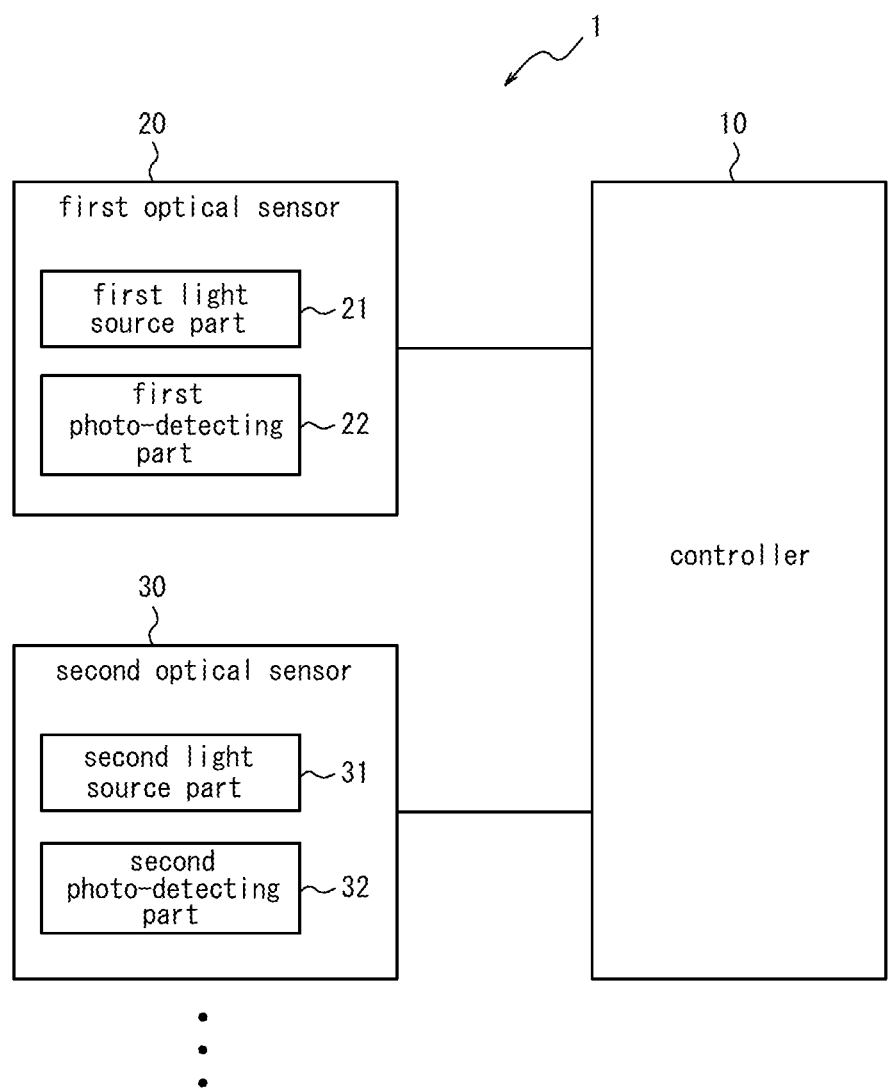
FIG. 1 is a function block diagram illustrating a basic configuration of a measurement apparatus according to an embodiment of this disclosure.

First, a basic configuration of a measurement apparatus 1 according to an embodiment of this disclosure will be described with reference to FIG. 1 before a specific embodiment example is described.

The measurement apparatus 1 includes a controller 10 and a plurality of sensors. The sensors include a first optical sensor 20 (first sensor) and a second optical sensor 30 (second sensor), but more sensors may be included. The controller 10, the first optical sensor 20 and the second optical sensor 30 may each be placed in a separate housing. Signals can be transmitted/received between the controller 10 and the first optical sensor 20 and the second optical sensor 30 over wire or wireless communication means. The controller 10 may be placed in the same housing of either the first optical sensor 20 or the second optical sensor 30.

The controller 10 is configured to acquire an output value of each of the first optical sensor 20 and the second optical sensor 30. The controller 10 is configured by including at least one processor.

In an embodiment, the processor includes one or more circuits or units configured to execute instructions stored in a related memory, for example, to execute one or more data calculation procedures or processing. In the other embodiment, the processor may be a firmware (e.g. a discrete logic component) configured to execute one or more data calculation procedures or processing.

According to various embodiments, the controller 10 includes one or more processors, microprocessors, microcontrollers, Application Specific Integrated Circuits (ASICs), Digital Signal Processors (DSPs), Programmable Logic Devices (PLDs), Field-Programmable Gate Arrays (FPGAs) or any combination of these devices or configurations or a combination of other known devices or configurations.

The controller 10 may include a memory embedded in the processor or a memory separated from the processor. The controller 10 can execute a program that specifies control procedures. The controller 10 may be configured to read a program recorded on a non-transitory computer-readable medium into memory to implement it.

The first optical sensor 20 and the second optical sensor 30 are sensors configured to optically measure the biological information of the user. The measurement apparatus 1 according to this embodiment can measure the same type of biological information by using the first optical sensor 20 and the second optical sensor 30. The first optical sensor 20 and the second optical sensor 30 output an output value for calculating the biological information. The biological information to be measured may include at least one of oxygen saturation, pulse, blood flow and blood flow velocity. The measurement apparatus 1 according to this embodiment can measure, as a value that indicates the subject's oxygen saturation, percutaneous arterial oxygen saturation ($SpO_2$, in which S stands for Saturation, P stands for Percutaneous or Pulse Oximetry, and $O_2$ stands for Oxygen), for example. Hereinafter the percutaneous arterial oxygen saturation ($SpO_2$) is merely referred to also as oxygen saturation. It is to be noted that values indicating the oxygen saturation include $SaO_2$ (in which S stands for Saturation, a stands for artery and $O_2$ stands for Oxygen), which indicates an actual measured value of arterial oxygen saturation. $SpO_2$ is a method of indirectly measuring $SaO_2$. They take approximate values if measurement conditions are satisfied.

The first optical sensor 20 includes a first light source part 21 and a first photo-detecting part 22. The first light source part 21 includes one or more light sources. As a light source, Light Emitting Diode (LED), Laser Diode (LD), Vertical Cavity Surface Emitting Laser (VCSEL), Distributed Feedback (DFB) laser, Fabry-Perot (FP) laser can be adopted. The first light source part 21 emits, as measurement light, light that can detect specific components contained in the blood, for example.

The first photo-detecting part 22 includes one or more photodetectors. The photodetectors include those using external photoelectric effect and those using internal photoelectric effect. The photodetectors using the external photoelectric effect include a Photo Multiplier Tube (PMT). The photodetectors using internal photoelectric effect include a photodiode (PD) that uses photoelectromotive force effect, an Avalanche Photodiode (APD) and a phototransistor. The output value of the photodetector is saturated when it receives light of more than a predetermined light quantity. When the output value is saturated, the output value does not change or changes only slightly even if it receives more intense light. As a result, the measurement apparatus 1 cannot precisely measure the biological information on the basis of the output of the first photo-detecting part 22. Measurement by the photodetector uses an area where output value changes approximately linearly according to the light quantity before the output value is saturated.

The second optical sensor 30 includes a second light source part 31 and a second photo-detecting part 32. The second light source part 31 and the second photo-detecting part 32 are configured in the same manner as the first light source part 21 and the first photo-detecting part 22 of the first optical sensor 20 and act in the same manner.

The first optical sensor 20 and the second optical sensor 30 can be worn on different parts of the body of the user. The different parts of the user are parts directing different directions of the body of the user. The different parts of the user include, for example, right and left sides of the head, front and back sides of the head, right and left arms, back of the hand, palm and the like. In this manner, when the first optical sensor 20 receives direct rays of the sun, the second optical sensor 30 is more likely not to receive direct rays of the sun (and vice versa). Therefore, either the first optical sensor 20 or the second optical sensor 30 is more likely to measure the biological information normally. The first optical sensor 20 and the second optical sensor 30 can be worn on ears, neck, back of the head, temples, forehead, arms, wrists, fingers, stomach, waist, thighs, feet, ankles, toes, and other parts.

The controller 10 receives output values from a plurality of sensors including the first optical sensor 20 and the second optical sensor 30. The controller 10 selects any one of sensors on the basis of the output values of each of the sensors, and determines the measurement value of the biological information on the basis of the output value of the selected sensor. For example, the controller 10 can determine, on the basis of the output value acquired from the first photo-detecting part 22 or the second photo-detecting part 32, that any one of the photodetectors receives light of equal to or greater than a predetermined light quantity and is saturated. In that case, the controller 10 eliminates the first optical sensor 20 or the second optical sensor 30 that includes the photodetector from the objects of selection.

[Examples of Specific Configuration]

Figure 2:
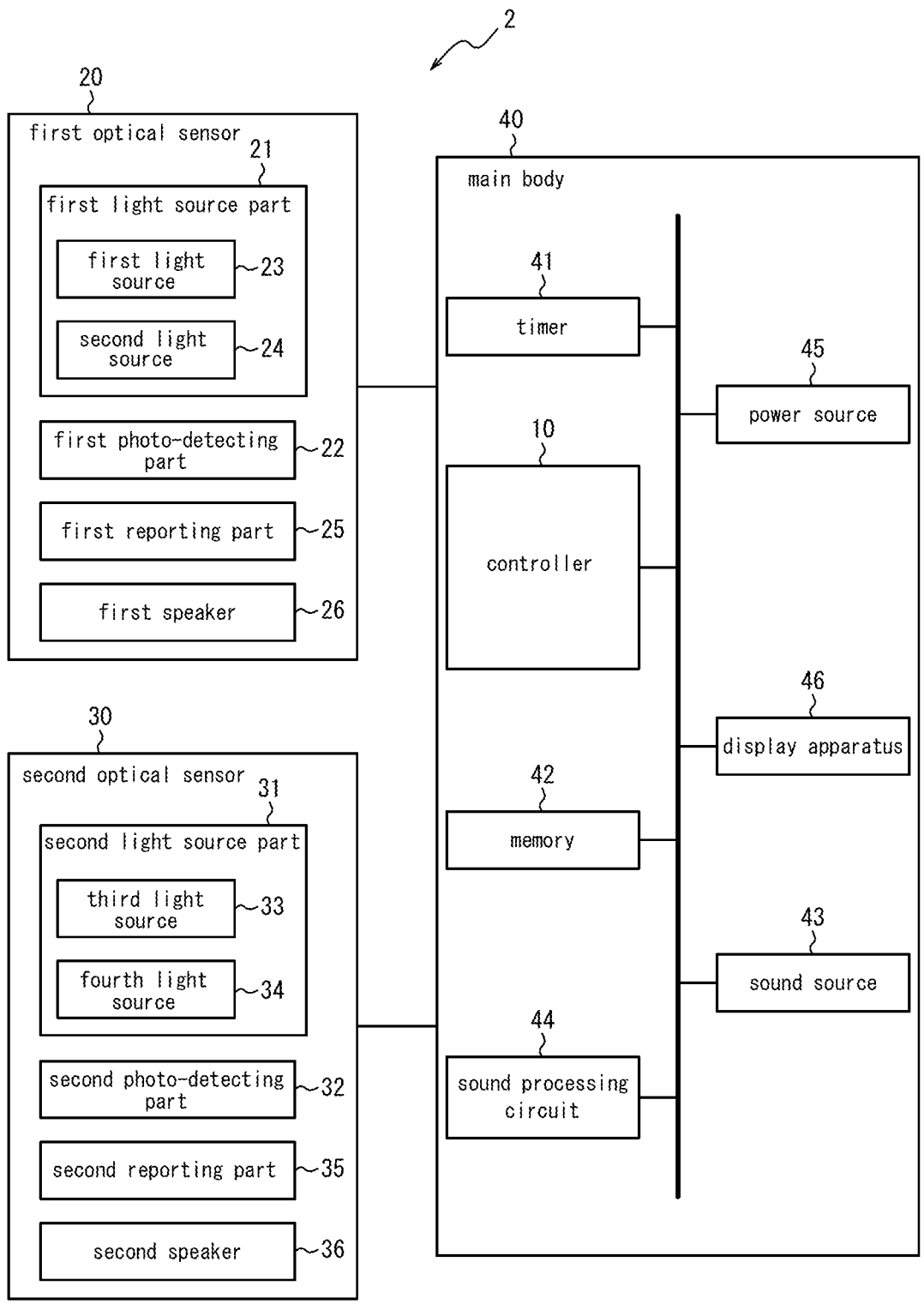
FIG. 2 is a function block diagram illustrating more specific configuration of the measurement apparatus according to an embodiment.

Next, more specific configuration example of the measurement apparatus 2 according to an embodiment will be described with reference to FIGS. 2 to 6. It is to be noted that the controller 10, the first optical sensor 20 and the second optical sensor 30 in FIG. 2 have the same configurations and actions as those of the corresponding components of the measurement apparatus 1 described by using FIG. 1 and additional configurations and functions The measurement apparatus 2 is an apparatus with a built-in bone conduction headphone configured to measure the biological information. In this embodiment, the measurement apparatus 2 measures the oxygen saturation ($SpO_2$). As illustrated in FIG. 2, the measurement apparatus 2 includes the first optical sensor 20, the second optical sensor 30 and a main body 40 having the controller 10.

Figure 3:
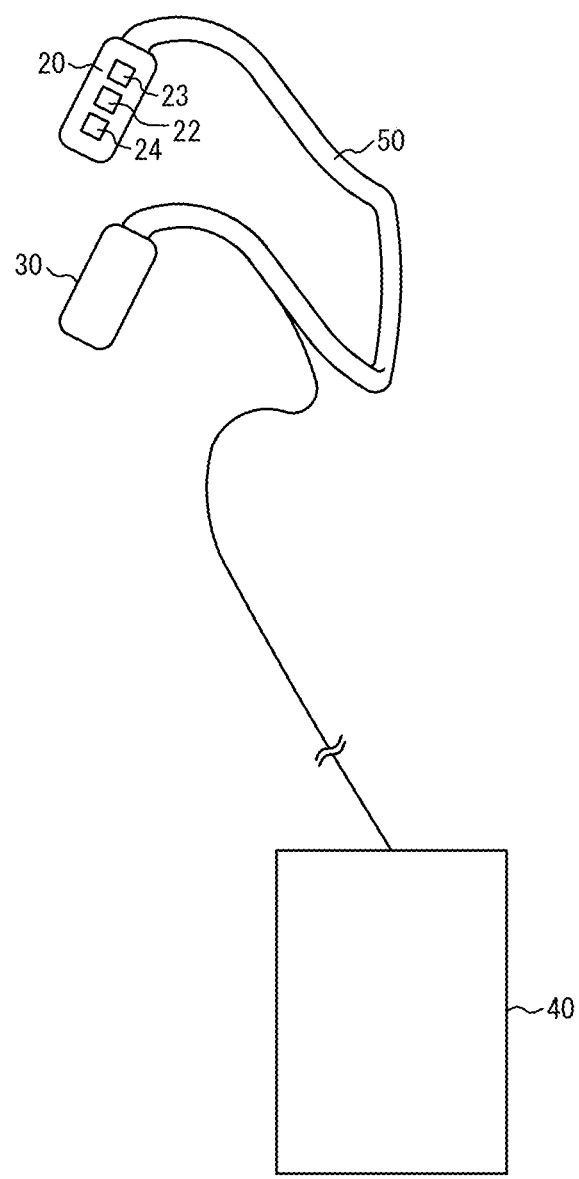
FIG. 3 is a perspective view of the measurement apparatus in FIG. 2.

FIG. 3 describes an overall schematic configuration of the measurement apparatus 2. The first optical sensor 20 and the second optical sensor 30 are connected by a flexible neck band 50 (fixing member). Further, the main body 40 is provided separately from the first optical sensor 20 and the second optical sensor 30. The main body 40 is electrically connected to the first optical sensor 20 and the second optical sensor 30 by a line.

Figure 4:
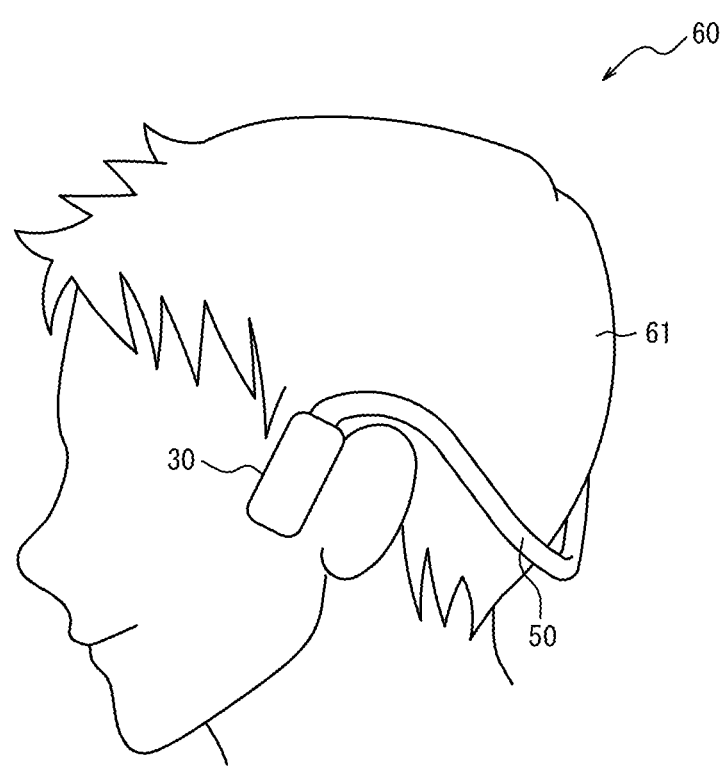
FIG. 4 is a diagram illustrating a state where the measurement apparatus in FIG. 3 is worn on a user's head.

As illustrated in FIG. 4, the measurement apparatus 2 is fixed to a head 61 of a user 60 by using a neck band 50. The neck band 50 includes a curved part near each end thereof such that it can be hooked on the right and left ears. The neck band 50 also includes a large curve at its center, and the curve wraps around the back of the head 61 and connects the portion hooked on the left ear and that hooked on the right ear with the measurement apparatus 2 worn on the head 61 of the user 60. The neck band 50 is formed of an elastic member, and the first optical sensor 20 is abutted against the right side head of the user 60 and the second optical sensor 30 is abutted against the left side head of the user 60 with the measurement apparatus 2 worn on the head 61 of the user 60. In this state, the first optical sensor 20 and the second optical sensor 30 are pressed against the head 61 of the user 60. In this manner the neck band 50 fixes the first optical sensor 20 and the second optical sensor 30 in a stable manner to the positions corresponding respectively to the right ear and the left ear of the user 60.

(Optical Sensor)

As illustrated in FIG. 2, the first optical sensor 20 includes a first light source part 21, a first photo-detecting part 22, a first reporting part 25 and a first speaker 26.

Figure 5:
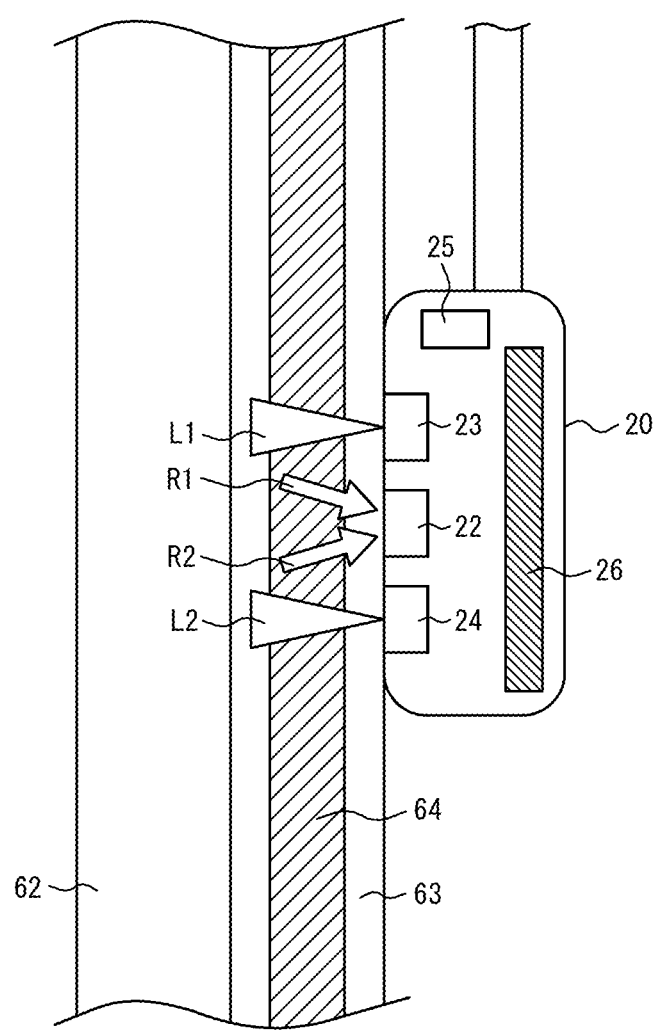
FIG. 5 is a diagram illustrating a physical configuration of a first optical sensor and a measurement method.

The first light source part 21 includes a first light source 23 and a second light source 24. The first light source 23 and the second light source 24 are disposed across the first photo-detecting part 22 as illustrated in FIGS. 3 and 5.

The first light source 23 and the second light source 24 emit, as measuring beam, light of a wavelength capable of detecting the amount of hemoglobin bonded to oxygen contained in the blood. The first light source 23 and the second light source 24 may be configured as an LED light source, for example.

The first light source 23 and the second light source 24 emit light of wavelengths different from each other. The first light source 23 emits light of a first wavelength having a large difference between the optical absorbance of hemoglobin bonded to oxygen (hereinafter referred to as "oxygenated hemoglobin") and the optical absorbance of hemoglobin not bonded to oxygen (hereinafter referred to as "reduced hemoglobin"). The first wavelength is a wavelength of 600 nm to 700 nm, for example. The light emitted from the first light source 23 is what is called red light. In this embodiment, explanation will be given assuming that the first wavelength is 660 nm.

The second light source 24 emits light of a second wavelength having a difference between the optical absorbance of oxygenated hemoglobin and that of reduced hemoglobin smaller than that of the first wavelength. The second wavelength is what is called near infrared light of a wavelength from 800 nm to 1000 nm, for example. In this embodiment, explanation will be given assuming that the second wavelength is 850 nm.

The first photo-detecting part 22 can use various photo-detectors. In this embodiment, the first photo-detecting part 22 is composed of a photodiode (PD).

A measurement method of $SpO_2$ using the first optical sensor 20 will be described with reference to FIG. 5. FIG. 5 illustrates a state where the first light source 23, the second light source 24 and the first photo-detecting part 22 of the first optical sensor 20 are abutted against near the anterior to the right ear of the user 60 (in the direction in which the face of the user 60 is directed). A skull 62 is located directly beneath the skin of a detected part 63 of the user 60. The first optical sensor 20 measures the amount of $SpO_2$ of the blood passing through a superficial temporal artery 64 of the detected part 63. It is to be noted that the superficial temporal artery 64 is an example. The blood streams to be measured are not limited to those of the superficial temporal artery 64.

Figure 6:
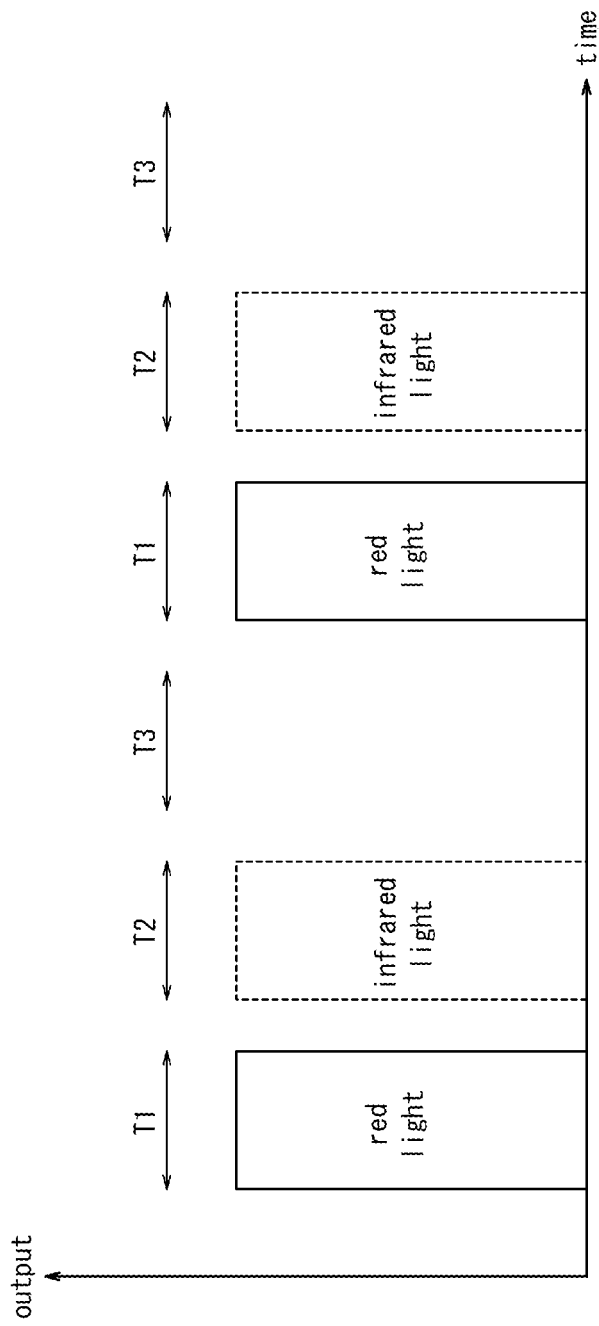
FIG. 6 is a timing chart illustrating a light source output of a first light source part.

The first light source 23 and the second light source 24 emit light L1 (red light) of a first wavelength and light L2 (near infrared light) of a second wavelength to the skull 62. FIG. 6 is a diagram illustrating a timing of emitting light of a first wavelength by the first light source 23 (solid line) and a timing of emitting light of a second wavelength by the second light source 24 (broken line). The time period T1 during which the first light source 23 emits light and the time period T2 during which the second light source 24 emits light are sequentially repeated at predetermined time intervals such that T1 and T2 are not duplicated to each other. Furthermore, the time period T3 during which both the first light source 23 and the second light source 24 are not operated can be provided between the time period T2 and the time period T1.

As illustrated in FIG. 5, reflected light R1, which is a part of the reflected light of light L1 of the first wavelength reflected by the skull 62 passes through the superficial temporal artery 64 and is detected by the first photo-detecting part 22. In the same manner, reflected light R2, which is a part of the reflected light of light L2 of the second wavelength reflected by the skull 62 passes through the superficial temporal artery 64 and is detected by the first photo-detecting part 22. These reflected lights R1 and R2 receive absorption according to its wavelength when passing through the superficial temporal artery 64.

The first reporting part 25 illustrated in FIGS. 2 and 5 emits a stimulus to the user 60 under the control of the controller 10. The first reporting part 25 can emit a stimulus by any of sound, vibration, light and electricity or a combination of two or more of them. When a stimulus by sound is emitted, for example, the first reporting part 25 can emit a warning sound to the user 60 by using the first speaker 26 described below. When a stimulus by vibration is emitted, the first reporting part 25 includes a vibrating motor, and a stimulus can be emitted by vibrating the vibrating motor. The first reporting part 25 has a luminous body that emits light forward, which is within eyesight of the user 60, and when a warning by light is emitted, the first reporting part 25 blinks the luminous body to emit a stimulus.

The first speaker 26 is a bone-conducting speaker configured to receive a signal from the main body 40 side and transmit sound such as music, as vibration, to the skull 62 of the user 60. The first speaker 26 is formed integrally with the first optical sensor 20. As illustrated in FIG. 5, in this embodiment, the first speaker 26 is located on the side opposite the side where the first light source 23, the second light source 24 and the first photo-detecting part 22 abut against the detected part 63. The first speaker 26 may be disposed at the other positions without being limited at the position illustrated in FIG. 5 as long as it can transmit sound to the user 60.

As illustrated in FIG. 2, the second light source part 31 of the second optical sensor 30 includes a third light source 33 and a fourth light source 34. The third light source 33 and the fourth light source 34 can be configured in the same manner as the first light source 23 and the second light source 24, respectively, of the first light source part 21, and thus the description thereof is omitted. Further, the second photo-detecting part 32, the second reporting part 35 and a second speaker 36 of the second optical sensor 30 can be configured in the same manner as the first photo-detecting part 22, the first reporting part 25 and the first speaker 26, respectively, of the first optical sensor 20, and the description thereof is omitted.

It is to be noted that it is not necessary to provide both the first reporting part 25 and the second reporting part 35, and either one may be provided. Further, instead of disposing the first reporting part 25 in the first optical sensor 20 and disposing the second reporting part 35 in the second optical sensor 30, a reporting part may be disposed in the main body 40. For example, a reporting part may be disposed in the main body 40, and a warning can be emitted from the main body 40 to the user 60 by warning sound, vibration, warning display on the display apparatus 46 and the like.

(Main Body)

Next, the main body 40 will be described with reference to FIG. 2. In addition to the controller 10, the main body 40 includes a timer 41, a memory 42, a sound source 43, a sound processing circuit 44, a power source 45 and a display apparatus 46. Each component of the main body 40 is electrically connected to each other by signal lines.

As described with reference to FIG. 1, the controller 10 acquires output values from the first optical sensor 20 and the second optical sensor 30 to determine the measuring value of the biological information, and in addition to that, controls the first optical sensor 20, the second optical sensor 30 and the main body 40. Processing executed by the controller 10 will be described below.

The timer 41 is a clock means configured to measure elapsed time from a predetermined event. When the controller 10 starts the timer 41, the timer 41 measures a predetermined time period and measurement is stopped. The predetermined time period is a few seconds, for example. The timer 41 is not necessary an independent component. The timer 41 may use a clock built in the controller 10.

The memory 42 includes a primary storage and a secondary storage. The memory 42 may be configured by using a semiconductor memory, a magnetic memory and an optical memory and the like, for example. The semiconductor memory may include a volatile memory and a non-volatile memory. The magnetic memory may include a hard disc, a magnetic tape and the like, for example. The optical memory may include Compact Disc (CD), Digital Versatile Disc (DVD) and Blu-ray Disc® (BD), for example. The memory 42 may be used for the controller 10 to store measured values or for storing programs executed by the controller 10. For example, the memory 42 may store program for estimating development an altitude disease from the measured values of $SpO_2$. The memory 42 may store the music data regenerated by the sound source 43.

The sound source 43 and the sound processing circuit 44 provide, with the first speaker 26 and the second speaker 36, a function as an acoustic apparatus. The sound source 43 outputs output signals such as music and the like. The sound processing circuit 44 has a function of processing sound signals output from the sound source 43. For example, the sound processing circuit 44 converts frequency of each frequency band and adjusts volume with respect to input sound signal and sends a resulting signal to the first speaker 26 and the second speaker 36. It is to be noted that the sound source 43 and the sound processing circuit 44 may be separated from the main body 40.

If the measurement apparatus has only the biological information measuring function, it may be difficult to motivate the user 60 to continuously wear the measurement apparatus. The measurement apparatus 2 according to this embodiment has the first speaker 26, the second speaker 36, the sound source 43 and the sound processing circuit 44, thus has a function as a music player, for example. The user 60 can enjoy music while continuously wearing the measurement apparatus 2. With the above described function, the measurement apparatus 2 can continuously measure $SpO_2$ of the user 60.

The power source 45 is a battery configured to provide electricity to each part of the main body 40 and each part of the first optical sensor 20 and of the second optical sensor 30 under control of the controller 10. It is to be noted that each of the first optical sensor 20 and the second optical sensor 30 may have its built-in battery without receiving electricity from the power source 45.

The display apparatus 46 may be various display apparatuses. For example, the display apparatus 46 is Liquid Crystal Display (LCD), Organic Electro-Luminescence Display (OELD) or Inorganic Electro-Luminescence Display (IELD). The display apparatus 46 can display a measured value of $SpO_2$. Furthermore, the display apparatus 46 adopts a touch panel to display music provided by the first speaker 26 and the second speaker 36, and allows the user 60 to select music to listen.

The controller 10 calculates $SpO_2$ at the detected part 63 on the basis of the output of the first photo-detecting part 22 and/or the second photo-detecting part 32 (i.e. a photoelectric signal of transmitted light). The measurement principle of $SpO_2$ by the controller 10 will be described by taking the first optical sensor 20 as an example.

In the blood, it is easy for the reduced hemoglobin to absorb light of a first wavelength, which is red light, and it is difficult for it to absorb light of a second wavelength, which is near infrared light. On the other hand, it is difficult for the oxygenated hemoglobin to absorb both the first wavelength light, which is red light, and the second wavelength light, which is near infrared light. That is, the light of a first wavelength, which is red light, is easy to be absorbed by the reduced hemoglobin and is difficult to be absorbed by the oxygenated hemoglobin. Further, the light of a second wavelength light, which is near infrared light, is difficult to be absorbed by the reduced hemoglobin and the oxygenated hemoglobin.

Therefore, on the basis of comparison between the light-receiving intensity at the first photo-detecting part 22 with respect to the light quantity of the light of a first wavelength emitted by the first light source 23 and the light-receiving intensity at the first photo-detecting part 22 with respect to the light quantity of the light of a second wavelength emitted by the second light source 24, a ratio between the oxygenated hemoglobin and the reduced hemoglobin in the blood can be calculated. The controller 10 can calculate $SpO_2$ on the basis of a ratio between the oxygenated hemoglobin and the reduced hemoglobin. In particular, supposing that the amount of oxygenated hemoglobin is $HbO_2$ and the amount of reduced hemoglobin is Hb, $SpO_2$ is calculated using the formula of $\{HbO_2/(Hb+HbO_2)\}\times 100$. The controller 10 calculates $SpO_2$ by using this formula, for example.

The controller 10 selects any one of the output values from the output values of the first optical sensor 20 and the second optical sensor 30, and determines the measured value of $SpO_2$ on the basis of the selected output value. For example, when the output value from the first optical sensor 20 is equal to or greater than a predetermined threshold and the light quantity received by the first photo-detecting part 22 is determined to exceed a predetermined light quantity, the controller 10 eliminates the first optical sensor 20 from the objects of selection. The predetermined light quantity is light quantity by which a photodiode of the first photo-detecting part 22 comes close to a saturated state. It is to be noted that, when the first photo-detecting part 22 outputs by inverting the output of the photodiode, the controller 10 determines that the light quantity received by the first photo-detecting part 22 exceeds a predetermined light quantity when the output value is equal to or smaller than a predetermined threshold. When the controller 10 determines that the output value from the second optical sensor 30 exceeds the predetermined light quantity, it eliminates the second optical sensor 30 from the objects of selection.

When the sensor whose output value is selected to be used for determining the measured value is changed from the first optical sensor 20 to the second optical sensor 30, the controller 10 may start the timer 41 to monitor such that the first optical sensor 20 will not be selected again within a predetermined time period. The predetermined time period may be a few seconds, for example. When the sensor from which the output value is selected is changed from the second optical sensor 30 to the first optical sensor 20, it is also possible to monitor such that the second optical sensor 30 will not be selected within a predetermined time period in the same manner. In this manner, a phenomenon in which a sensor to be selected is switched repeatedly at high speed within an extremely short time period can be avoided.

Instead of the above described determination using a threshold, the controller 10 may calculate the S/N ratio of the measured value of the biological information on the basis of the output values of the first optical sensor 20 and the second optical sensor 30 and adopt the output value of a better S/N ratio. In FIG. 6, the output value acquired from the first photo-detecting part 22 in the time period T3 during which both the first light source 23 and the second light source 24 do not emit light in FIG. 6 may be determined as a noise (N). The controller 10 can determine the difference between the output value acquired from the first photo-detecting part 22 in the time period T1 during which the first light source 23 emits light and the output value acquired from the first photo-detecting part 22 in the time period T2 during which the second light source 24 emits light as a signal (S). In the same manner, the controller 10 can calculate the noise (N) and the signal (S) with respect to the second optical sensor 30.

The controller 10 can determine that the biological information cannot be measured when the output values of both of the first optical sensor 20 and the second optical sensor 30 are equal to or greater than a predetermined light quantity. The controller 10 can determine that the biological information cannot be measured when the S/N ratios of both of the first optical sensor 20 and the second optical sensor 30 are lower than a predetermined threshold. For example, when the solar elevation is high and the sunlight hits right above the head, a plurality of sensors may be unusable at the same time.

When the controller 10 determines that the biological information cannot be measured, it sends a signal to at least one of the first reporting part 25 and the second reporting part 35 and gives a stimulus to the user 60. When the biological information cannot be measured, the user 60 may face the other direction or move outdoor to be in a measurable state.

The controller 10 may estimate the possibility that the subject may develop an altitude disease (altitude disorder) on the basis of SpO$_2$ acquired from the measurement. Reduction in SpO$_2$ makes the subject more susceptible to the altitude disease. When the altitude disease is estimated to be developed, the controller 10 may send a signal to both or either one of the first reporting part 25 and the second reporting part 35 to issue a warning to the user 60. When the altitude disease is estimated to be developed, a reporting method different from that used for the case where the biological information cannot be measured described above may be used. For example, a stimulus generating pattern when reporting with sound, light, vibration, electricity and the like can be changed.

The main body 40 can use hardware dedicated to the measurement apparatus 2, but not limited thereto. As the main body 40, a smart phone or a portable digital assistant may be used. In that case, functions of the measurement apparatus 2 according to this disclosure can be provided as software read by a smart phone or a portable digital assistant.

[Measurement Processing]

Next, the measurement processing executed by the controller 10 will be described.

Example 1

Figure 7:
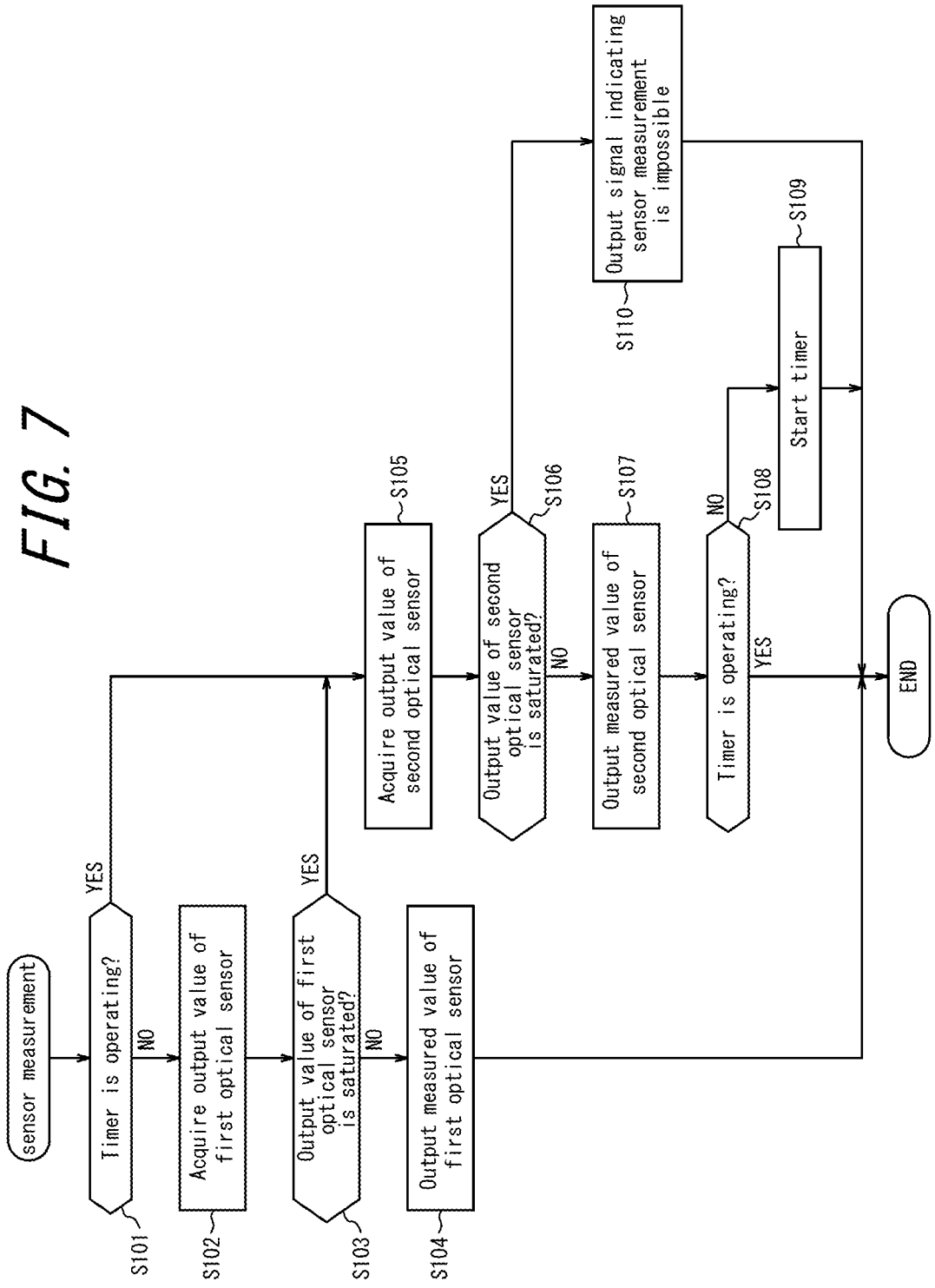
FIG. 7 is a flow chart illustrating a first example of processing executed by a controller.

Example 1 of the measurement processing executed by the controller 10 will be described with reference to the flow chart in FIG. 7. The processing of the flow chart in FIG. 7 is repeated sequentially, not only once.

First, the controller 10 confirms if the timer 41 is operating (step S101). When a sensor, which is an object used for determining the measured value, is switched from the first optical sensor 20 to the second optical sensor 30, the timer 41 is used as a clock means configured to prevent a sensor which is an object used for determining the measured value from being switched again to the first optical sensor 20 within a predetermined time period.

When the timer 41 is not operating (No in step S101), the controller 10 acquires the output value of the first optical sensor 20 (step S102). Acquisition of the output value includes at least one cycle or more of the time periods T1 and T2 in FIG. 6. In the time period T1, the first light source 23 emits light L1 of a first wavelength and the first photo-detecting part 22 detects reflected light R1 of light L1 of a first wavelength. In the time period T2, the second light source 24 emits light L2 of a second wavelength and the first photo-detecting part 22 detects reflected light R2 of light L2 of a second wavelength. The first photo-detecting part 22 converts the detected light into an electrical signal by photoelectric conversion and transmits the signal to the controller 10 of the main body 40.

When the output value of the electrical signal of the time period T1 or T2 acquired from the first optical sensor 20 is equal to or greater than a predetermined threshold, the controller 10 determines that the first optical sensor 20 is saturated. On the other hand, when the output value of the electrical signal of the time period T1 and the time period T2 is less than the predetermined threshold, the controller 10 determines that the first optical sensor 20 is not saturated (step S103).

When the first optical sensor 20 is not saturated (No in step S103), the controller 10 outputs the measured value of SpO$_2$ determined from the output value of the first optical sensor 20 (step S104) and ends sensor measurement. The output measured value is stored in the memory 42. The output measured value may be displayed on the display apparatus 46 provided to the main body 40.

When the timer 41 is operating in step S101 (Yes in step S101) and when the first optical sensor 20 is saturated in step S103 (Yes in step S103), the controller 10 acquires the output value of the second optical sensor 30 (step S105). As with the case of the first optical sensor 20, acquisition of the output value includes at least one or more cycles of the time period T1 and the time period T2 in FIG. 6. In the time period T1, the third light source 33 emits light of a first wavelength and the second photo-detecting part 32 detects reflected light of light of a first wavelength. In the time period T2, the fourth light source 34 emits light of a second wavelength and the second photo-detecting part 32 detects reflected light of light of a second wavelength. The second photo-detecting part 32 converts the detected light into an electrical signal by the photoelectric conversion and sends the signal to the controller 10 of the main body 40.

When the output value of the electrical signal of the time period T1 or the time period T2 acquired from the second optical sensor 30 is equal to or greater than a predetermined threshold, the controller 10 determines that the second optical sensor 30 is saturated. When the output value of the electrical signal of the time period T1 and the time period T2 acquired from the second optical sensor 30 is less than the predetermined threshold, the controller 10 determines that the second optical sensor 30 is not saturated (step S106).

When the second optical sensor 30 is not saturated (No in step S106), the controller 10 outputs the measured value of $SpO_2$ determined from the output value of the second optical sensor 30 (step S107). The output measured value is stored in the memory 42. The measured value may be displayed on the display apparatus 46 provided to the main body 40.

Next, the controller 10 detects whether the timer 41 is operating or not (step S108). When the timer 41 is operating (Yes in step S108), the controller 10 ends sensor measurement. When the timer 41 is not operating (No in step S108), the controller 10 starts the timer 41 (step S109) and after that ends sensor measurement.

When the second optical sensor 30 is saturated in step S106 (Yes in step S106), the controller 10 outputs a signal indicating that the sensor measurement is impossible (step S110). The signal indicating that the sensor measurement is impossible is transmitted to both of or either one of the first reporting part 25 of the first optical sensor 20 and the second reporting part 35 of the second optical sensor 30. Further, the controller 10 stores the fact that $SpO_2$ could not be measured in the memory 42. The controller 10 may display that measurement is impossible on the display apparatus 46 of the main body 40. After that the controller 10 ends sensor measurement.

The sensor measurement operation on the basis of the above described flow chart in FIG. 7 is executed repeatedly at intervals shorter than the operating period of the timer 41.

The above described processing allows the measurement apparatus 2 to measure $SpO_2$ by using an available sensor selected from the first optical sensor 20 and the second optical sensor 30. Normally sunlight is radiated from one direction, thus it is expected that at least one of the first optical sensor 20 and the second optical sensor 30 is available. Therefore, a measurement apparatus 2 having a higher availability can be provided. Further, if both the first optical sensor 20 and the second optical sensor 30 cannot measure, a stimulus is given to the user 60 by at least one of the first reporting part 25 and the second reporting part 35, which enables the user 60 to recognize that the measurement is impossible and to take measures such as facing the other direction to allow measurement. Furthermore, the timer 41 is provided to prevent the measured value from being switched repeatedly in a short time period between the first optical sensor 20 and the second optical sensor 30. In this manner, a stable measurement can be performed.

Example 2

Figure 8:
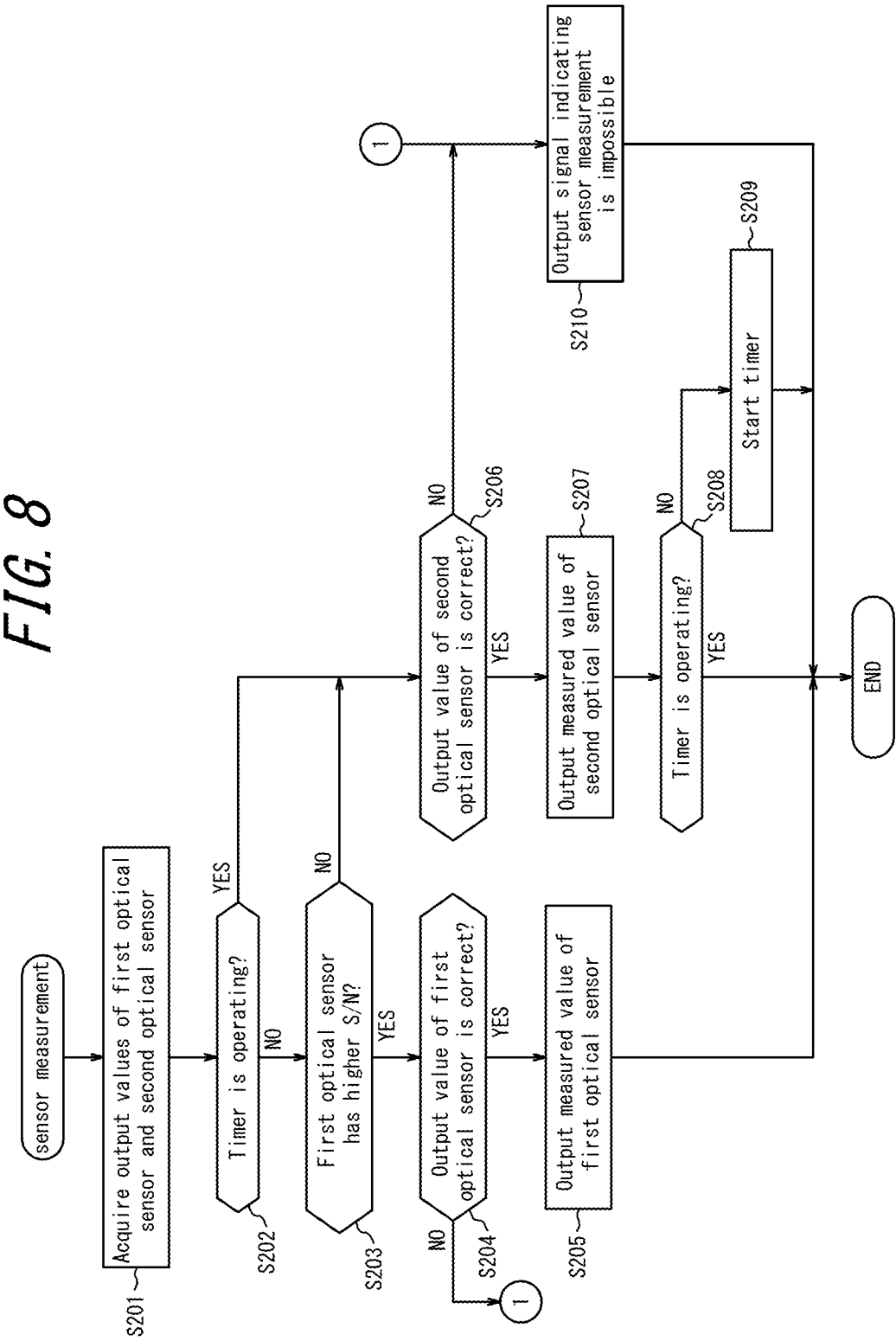
FIG. 8 is a flow chart illustrating a second example of processing executed by the controller.

Next, Example 2 of the measurement processing executed by the controller 10 will be described with reference to the flow chart in FIG. 8. The processing of the flow chart in FIG. 8 is partially similar to that in FIG. 7. Thus the description in common with the flow chart in FIG. 7 is omitted.

First, the controller 10 acquires output values from the first optical sensor 20 and the second optical sensor 30 (step S201). The controller 10 measures at least one cycle of the time periods from T1 to T3 in FIG. 6 with respect to both of the first optical sensor 20 and the second optical sensor 30.

Next, the controller 10 confirms if the timer 41 is operating (step S202).

When the timer 41 is not operating (No in step S202), the controller 10 determines whether or not the S/N ratio of the measured value of the first optical sensor 20 is higher than that of the measured value of the second optical sensor 30 (step S203).

When the S/N ratio of the first optical sensor 20 is higher than that of the second optical sensor 30 (Yes in step S203), the controller 10 determines whether or not the first optical sensor 20 outputs a correct output value (step S204). For example, the controller 10 determines whether or not the output value of the first optical sensor 20 is saturated. When the controller 10 determines that the output value of the first optical sensor 20 is saturated, it determines that a correct output value is not output.

When the controller 10 determines that a correct output value is output from the first optical sensor 20 (Yes in step S204), it outputs the measured value of $SpO_2$ by the first optical sensor 20 (step S205) and ends the process.

When the timer 41 is operating in step S202 (Yes in step S202), and the S/N ratio of the first optical sensor 20 is not higher than that of the second optical sensor 30 in step S203 (No in step S203), the controller 10 determines whether or not the second optical sensor 30 outputs a measure value correctly (step S206).

When the second optical sensor 30 outputs a correct output value (Yes in step 206), the controller 10 outputs the measured value of $SpO_2$ determined from the output value of the second optical sensor 30 (step S207).

In steps S208 and S209, the controller 10 processes in the same manner as steps S108 and S109 of Example 1 in FIG. 7 and ends the process.

When the controller 10 determines that a correct output value is not output from the first optical sensor 20 in step S204 (No in step S204) and a correct output value is not output from the second optical sensor 30 in step S206 (No in step S206), the controller 10 outputs a signal indicating that the sensor measurement is impossible (step S210).

According to the above described processing of Example 2, the measurement apparatus 2 can adopt a measured value having a higher S/N ratio from the measured values of $SpO_2$ of the first optical sensor 20 and the second optical sensor 30. Thus a measured value of a sensor with a higher reliability can be used.

Example 3

Figure 9:
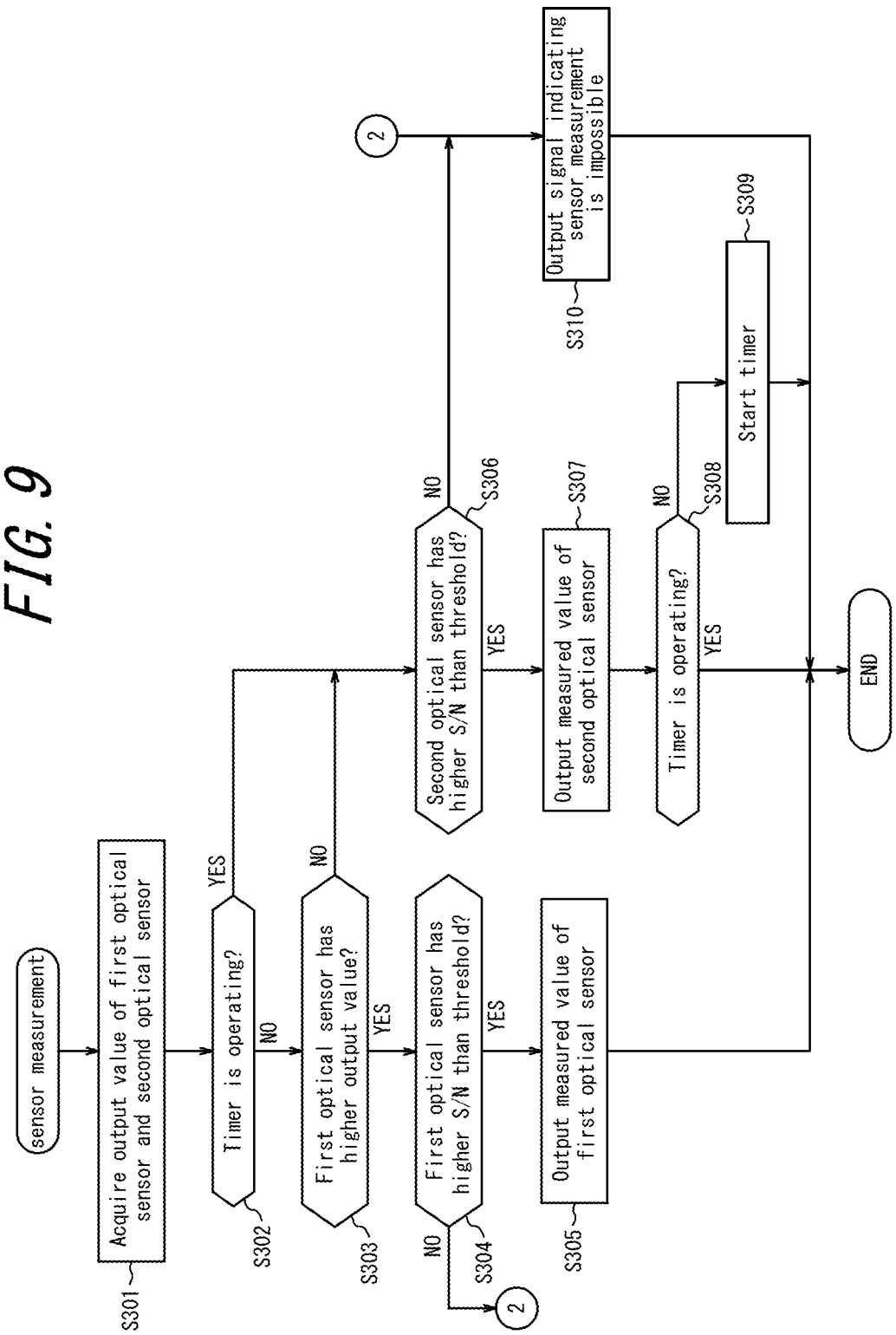
FIG. 9 is a flow chart illustrating a third example of processing executed by the controller.

Example 3 of the measurement processing executed by the controller 10 will be described with reference to the flow chart in FIG. 9. The processing of steps S301, S302, S305 and S307 to S310 of the flow chart in FIG. 9 are the same as those of steps S201, S202, S205 and S207 to S210 of the flow chart in FIG. 8, respectively, and thus the description thereof is omitted.

In step S303, the controller 10 compares the output value of the first optical sensor 20 with the output value of the second optical sensor 30 (step S303).

When the output value of the first optical sensor 20 is larger than that of the second optical sensor 30 (Yes in step S303), the controller 10 determines whether or not the S/N ratio of the output value of the first optical sensor 20 is equal to or greater than a predetermined threshold (step S304).

When the S/N ratio of the output value of the first optical sensor 20 is less than the predetermined threshold (Yes in step S304), the controller 10 outputs the measured value of the first optical sensor 20 (step S305).

When the timer 41 is operating in step S302 (Yes in step S302) and when the output value of the first optical sensor 20 is not greater than the output value of the second optical sensor 30 in step S303 (No in step S303), the controller 10 proceeds to step S306. When the S/N ratio of the measured values of the second optical sensor 30 is equal to or greater than the predetermined threshold in step S306 (Yes in step S306), the controller 10 proceeds to step S307.

When the S/N ratio of the first optical sensor 20 is less than the predetermined threshold in step S304 (No in step S304) and when the S/N ratio of the second optical sensor 30 is less than the predetermined threshold in step S306 (No in step S306), the controller 10 proceeds to step S310.

According to the above described processing of Example 3, among the first optical sensor 20 and the second optical sensor 30, measurement can be made on the basis of a sensor that can obtain a larger detection value.

[Variation]

Figure 10:
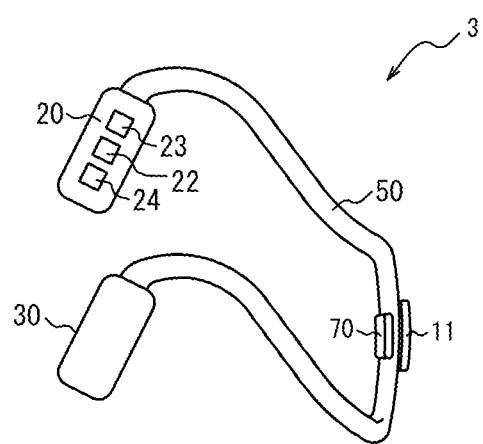
FIG. 10 is a perspective view of a measurement apparatus according to a variation.

FIG. 10 illustrates a measurement apparatus 3 as a variation of the measurement apparatus 2. In the measurement apparatus 3, a controller 11 is attached, with other components of a main body 40, to a part of a neck band 50. Further, the measurement apparatus 3 includes a third optical sensor 70. The optical sensor 70 abuts against the back of the neck of the user 60, for example, with the measurement apparatus 3 worn on the user 60. As with the first optical sensor 20 and the second optical sensor 30, the third optical sensor 70 has a light source part and a light detecting part, and measures $SpO_2$ of blood flowing through any vessel of the user 60.

According to the measurement apparatus 3 of the variance, a compact and easy-to handle measurement apparatus 3 can be provided. Further, even in the case where $SpO_2$ cannot be measured by both of the first optical sensor 20 and the second optical sensor 30, measurement can be made by using the third optical sensor 70. Therefore, a measurement apparatus 3 having a higher availability can be realized.

Although the embodiment according to this disclosure has been described on the basis of the drawings and the examples, it is to be understood that various changes and modifications may be made easily on the basis of this disclosure by those who are ordinarily skilled in the art. Accordingly, such changes and modifications are included in the scope of the disclosure herein. For example, functions and the like included in each component, each step and the like may be rearranged without logical inconsistency. A plurality of components or steps can be combined into one or divided. The embodiment according to this disclosure can be realized as a method or program executed by a processor provided to the apparatus, or a storage medium that stores program. It is to be understood that they are included in the scope of this disclosure.

In this disclosure, descriptions of "first" and "second" are identifiers for distinguishing configurations. In the configurations distinguished by the descriptions of "first" and "second" and the like, the numbers can be exchanged. For example, with respect to the first lens and the second lens, the identifiers of "first" and "second" can be exchanged. Exchange of identifiers is performed at the same time. The configurations are distinguished even after the identifiers are exchanged. Identifiers may be omitted. After identifiers are omitted, the configuration is distinguished by a reference sign. Order of the configuration and existence of low-numbered identifier shall not be determined only on the basis of description of identifiers such as "first" and "second" in this disclosure.

The invention claimed is:

1. A measurement apparatus comprising
   a plurality of sensors capable of being worn on different parts of a human body; and
   a controller configured to acquire an output value of each of a plurality of the sensors,
   wherein, when an output value of a sensor included in a plurality of the sensors indicates that a quantity of light received by the sensor is equal to or greater than a predetermined light quantity that saturates the sensor such that an output value from the sensor does not change or slightly changes when the sensor receives more intense light, the controller eliminates the sensor from sensors to be selected from the plurality of sensors, and
   wherein each of the sensors to be selected from the plurality of the sensors outputs an output value for calculating a same type of biological information by optical measurement, and the controller selects any one of the sensors to be selected on the basis of the output value of each of the sensors to be selected and determines a measured value of the biological information on the basis of an output value of the sensor selected.

2. The measurement apparatus according to claim 1, wherein, when output values of all sensors to be selected are indicated as being equal to or greater than the predetermined light quantity, the controller determines that the biological information cannot be measured.

3. The measurement apparatus according to claim 2, wherein the apparatus comprises a reporting part configured to emit a stimulus to a user, and the controller emits a stimulus to a user from the reporting part when the controller determines that the biological information cannot be measured.

4. The measurement apparatus according to claim 3, wherein the reporting part emits a stimulus by at least one of sound, vibration, light and electricity.

5. The measurement apparatus according to claim 1, wherein, the controller calculates a S/N ratio of a measured value of biological information acquired from each of the sensors to be selected on the basis of an output value of each of the sensors to be selected, and selects any one of the sensors to be selected having a S/N ratio greater than a predetermined threshold.

6. The measurement apparatus according to claim 5, wherein, when a S/N ratio of a measured value of biological information acquired from all sensors to be selected is equal to or smaller than a predetermined threshold, the controller determines that the biological information cannot be measured.

7. The measurement apparatus according to claim 6, wherein the apparatus comprises a reporting part configured to emit a stimulus to a user, and the controller emits a stimulus to a user from the reporting part when the controller determines that the biological information cannot be measured.

8. The measurement apparatus according to claim 7, wherein the reporting part emits a stimulus by at least one of sound, vibration, light and electricity.

9. The measurement apparatus according to claim 1, wherein, the controller is further configured to switch the sensor selected from a first sensor to a second sensor, wherein when the sensor selected is switched from the first sensor selected to the second sensor selected, the controller controls such that the first sensor selected is not selected again within a predetermined time.

10. The measurement apparatus according to claim 1, wherein the plurality of the sensors to be selected include a first sensor and a second sensor, and the apparatus comprises one or more fixing members configured to fix the first sensor and the second sensor respectively to a left ear and a right ear of a head of a user.

11. The measurement apparatus according to claim 10, further comprising: a first speaker and a second speaker formed integral with the first sensor and the second sensor, respectively; and a sound source configured to provide sound to the first speaker and the second speaker.

12. The measurement apparatus according to claim 1, wherein the sensor selected measures at least one of oxygen saturation and blood flow velocity.

13. A measurement method comprising the steps of:
wearing a plurality of sensors on different parts of a user, the sensors each being configured to perform optical measurement of a same type of biological information;
acquiring an output value of each of a plurality of the sensors;
selecting any one of the sensors on the basis of the output value, wherein, when an output value of a sensor indicates that a quantity of light received by the sensor is equal to or greater than a predetermined light quantity that saturates the sensor such that an output value from the sensor does not change or slightly changes when the sensor receives more intense light, the sensor is eliminated from sensors to be selected from the plurality of sensors; and
determining a measured value of the biological information on the basis of an output value of a sensor selected.

* * * * *